United States Patent [19]
Phimmasone

[11] Patent Number: 5,658,147
[45] Date of Patent: Aug. 19, 1997

[54] WORKING MODEL FOR PROSTHODONTIC PREPARATION OF A CROWN FOR INSTALLATION ON AN IMPLANT FIXTURE

[75] Inventor: Anopet Phimmasone, Springfield, Va.

[73] Assignee: Shopvest, Inc., Virginia Beach, Va.

[21] Appl. No.: 529,979

[22] Filed: Sep. 19, 1995

[51] Int. Cl.$^6$ .................................. A61C 11/00; A61C 9/00
[52] U.S. Cl. ............................. 433/213; 433/214; 433/173
[58] Field of Search .................................... 433/213, 214, 433/173, 74

[56] References Cited

U.S. PATENT DOCUMENTS

| | | |
|---|---|---|
| 3,153,283 | 10/1964 | Weissman ............................ 433/74 |
| 3,518,761 | 7/1970 | Susman et al. |
| 4,054,995 | 10/1977 | Yoshida . |
| 4,060,899 | 12/1977 | Sauter . |
| 4,398,884 | 8/1983 | der Avanessian ................. 433/74 |
| 4,744,753 | 5/1988 | Ross ................................. 433/173 |
| 4,801,264 | 1/1989 | Weissman .......................... 433/74 |
| 4,955,811 | 9/1990 | Lazzara et al. ................... 433/173 |
| 5,052,929 | 10/1991 | Seal ................................... 433/173 |

*Primary Examiner*—Cary E. O'Connor
*Attorney, Agent, or Firm*—Armstrong, Westerman, Hattori, McLeland & Naughton

[57] ABSTRACT

A method of producing a working model for preparation of a clinical crown for attachment to an implant fixture in the mouth of a patient is described in which a laboratory analog, on which the crown is mounted during preparation, is formed as an assembly including a fixed sleeve and a detachable pin and wherein the crown-receiving portion of the pin element of the assembly replicates the crown-receiving portion of the implant fixture. The analog sleeve is fixedly mounted in a base segment of the model so that the analog pin bearing a crown to be prepared threadedly connected thereto can be removed from and returned to mounted installation in the model by simple sliding movement between the pin and sleeve. Also described is the resultant working model construction and the particular analog elements which also form parts of the invention.

29 Claims, 9 Drawing Sheets

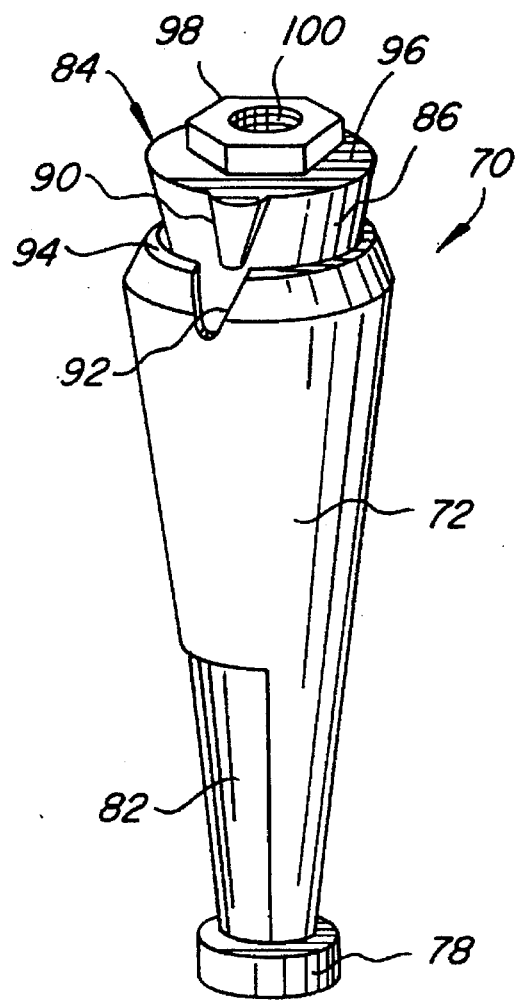
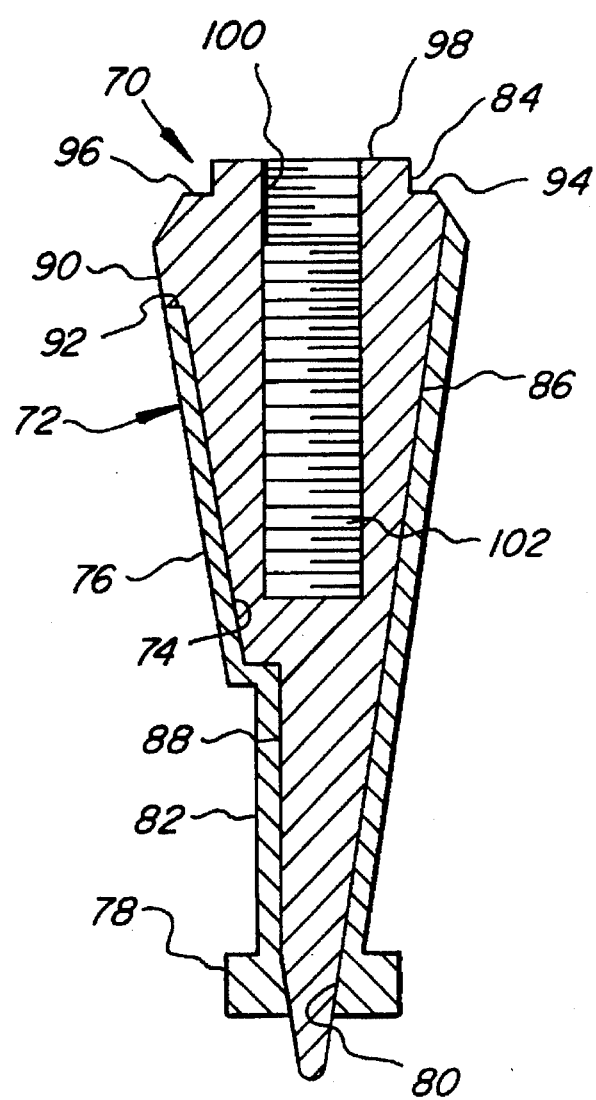
FIG. 7
FIG. 8

WORKING MODEL FOR PROSTHODONTIC PREPARATION OF A CROWN FOR INSTALLATION ON AN IMPLANT FIXTURE

BACKGROUND OF THE INVENTION

The present invention relates to the laboratory preparation of dental prostheses for installation on implant fixtures previously installed in the mouth of the patient. More particularly, the invention relates to the construction of a working model and the analog elements employed therein for use by a dental technician in the fabrication of restorative dental prostheses.

Dental prostheses which are fixedly attached to the jaw of a patient through the use of dental implants are common. Such prostheses employ implant fixtures which are permanently fused to the jaw of the patient, and crowns comprising abutments, upon which a prostheses is formed, for ultimate attachment to the implant fixture. Typically, a two-stage procedure is employed. In the first stage, an implant fixture is installed in a receptacle formed in the bone of the jaw of the patent and the fixture allowed to become bonded to the bone by osseointegration occurring over a period of several months. During the second stage of the procedure, the gum that overlies the now-fused implant fixture is incised to expose the top end of the fixture and a previously prepared crown is attached thereto by fitting the crown abutment to an abutment-receiving portion of the fixture and connecting the crown by means of a suitable screw that cooperates with a threaded socket in the implant fixture.

The description herein is directed principally to prostheses of the so-called "UCLA"-type in which the abutment is integrally-formed with the prosthesis casting. It should be understood, however, that the invention is equally applicable to standard abutment-cylinder assemblies in which the abutment is a separately formed element designed for threaded attachment to the fixture, as hereinafter described.

In preparing a dental prosthesis or crown for attachment to an implant fixture, a work holder, called a "working model", in the form of an accurate replica of the existing tooth and gum structure of the patient is made from molding material, such as die stone or plaster-of-paris. Such working model is utilized by the technician during the construction of the crown, which normally comprises a hard core or "abutment" that may be formed of metal, ceramic, plastic, or other hard material, and covered by a ceramic material, usually porcelain, or by plastic or composite materials that replicate the tooth or tooth group to be replaced. (In the description herein, the crown consists of two lower central teeth. The invention, however, contemplates crowns for replacing a single tooth, or groups of teeth, for the described or other regions of a patient's mouth.)

In essence, the working model is constructed by making an impression of the teeth and gums in the concerned region of the patient's mouth by enclosing them in dental impression material, as for example, silicone, or other formable rubber-like materials, to form a mold or "negative" into which molding material, such as plaster-of-paris, is placed and permitted to harden. The solidified model forms a work holder, sometimes termed, "a replica cast", which duplicates the affected region of the patient's dentition and within which the crown may be inserted during preparation in order to accurately determine its relationship to adjacent teeth for fitting purposes.

Presently, it is the practice in producing working models of the concerned type to make a single casting of molding material duplicating the patient's dentition and in which a laboratory analog is fixedly installed at the proper location. The upper end of the analog contains an internally threaded socket and an abutment-receiving portion that, in cooperation with the socket, enables a crown intended for ultimate attachment to an implant fixture to be set in the working model. Attachment of the crown to the laboratory analog is effected by passing a headed screw through an open-ended axial hole extending through the crown abutment and connecting it to an internally threaded socket in the analog. Typically, the screw employed for connecting the crown to the analog contains a slotted head for reception of a screw driving tool and is structurally similar to the screw employed for connecting the crown to the patient's implant fixture.

Thus, in preparing the crown, during the process of which the crown must be repeatedly removed and re-installed in place in the working model, it is necessary that the technician employ the screw driving tool to release the screw upon each removal of the crown from the working model and, conversely, to install the screw upon each mounting of the crown in place in the working model. This repeated manipulation of the screw each time the crown is removed or reinstalled on the working model is laborious and time-consuming and consequently adds substantially to the time and effort required for preparation of the crown. Furthermore, it increases the danger of eroding or otherwise damaging the cast working model.

It is, therefore, to the solution of this problem that the present invention is directed.

SUMMARY OF THE INVENTION

According to one aspect of the invention, therefore, there is provided a method for constructing a working model apparatus for use by a laboratory technician in the preparation of a prosthetic crown particularly intended for ultimate attachment to an implant fixture previously installed in the mouth of a patient comprising the steps of attaching a coping to the implant fixture mounted in the mouth of the patient; pouring dental impression material about the selected region of the mouth of the patient to enclose the coping and the region of the mouth on adjacent sides thereof to form an impression mold; removing an assemblage of the formed impression mold with the coping attached from the patient's mouth and connecting the assemblage to an impression tray; attaching to the exposed end of the coping an assembled separable implant fixture analog pin and sleeve assembly; packing molding material in the formed impression to a predetermined level leaving the analog sleeve exposed; permitting the mold material to solidify to produce a removable model segment; thereafter, placing additional molding material in the formed impression to substantially cover the exposed surface of the solidified removable model segment and the analog sleeve; permitting the additional molding material to solidify to produce a stationary model segment; removing the impression mold and the coping; and attaching a clinical crown to the pin element of the pin and sleeve assembly.

There is also provided by the invention, a working model apparatus of the heretofore described type comprising a stationary segment and a movable segment, both formed of a solidified molding material; the segments being connected for separation at a parting line therebetween; an analog sleeve containing an axial base fixedly secured on the stationary segment; an analog pin axially slidably received in the bore of the analog sleeve, the pin having an external shape adapted for snug, slidable reception in the sleeve bore and its upper end being formed to replicate a crown abutment-receiving portion of the implant fixture; and cooperable means on the pin and sleeve to prevent relative rotational movement between the pin and sleeve in their assembled condition.

The invention further contemplates a laboratory analog for installation in a working model utilized by a technician in the preparation of a crown intended for ultimate attachment to an implant fixture comprising a fixture analog sleeve having an external surface configured for locked retention in a body of solidified molding material in an axially-extending material bore; an analog pin having an external shape for snug, sliding reception to a predetermined extent in the bore of the analog sleeve; cooperating elements on the analog sleeve and the analog pin to prevent relative rotation therebetween; and an abutment-receiving portion on an exposed, crown-receiving end of the pin replicating the crown-receiving portion of the installed implant fixture, and means in the crown-receiving portion for attaching a clinical crown thereto, the means substantially replicating the means for attaching the crown to the implant fixture.

Pin and sleeve assemblies for use in working models in the preparation of dental prostheses are not new. Typical examples of prior art assemblies of this type are shown in U.S. Pat. Nos. 3,518,761, 4,054,995, 4,363,625, 4,801,264, and 4,955,811, in only the last of which is preparation of a crown for ultimate attachment to a previously installed implant fixture contemplated. Furthermore, nowhere in the prior art is there shown a method of constructing a working model in which an analog assembly installed in the model contains a pin whose abutment-receiving portion replicates the abutment-receiving portion of the implant fixture for which the crown is being prepared. Consequently, only from the present invention is there obtained the aforementioned benefits of rapid and effortless manipulation to and from a working model of a crown by a technician and of the avoidance of damage or erosion of the model during preparation of the crown prior to attachment to an implant fixture.

For a better understanding of the invention, its operating advantages, and the specific objections obtained by its use, reference should be made to the accompanying drawings and description which related to a preferred embodiment thereof.

BRIEF DESCRIPTION OF THE DRAWINGS

FIG. 7 is an enlarged perspective view of a typical laboratory implant analog assembly according to the present invention;

FIG. 8 is a sectional elevation view of the implant analog assembly shown in FIG. 7;

DESCRIPTION OF THE PREFERRED EMBODIMENTS OF THE INVENTION

Figure 1:
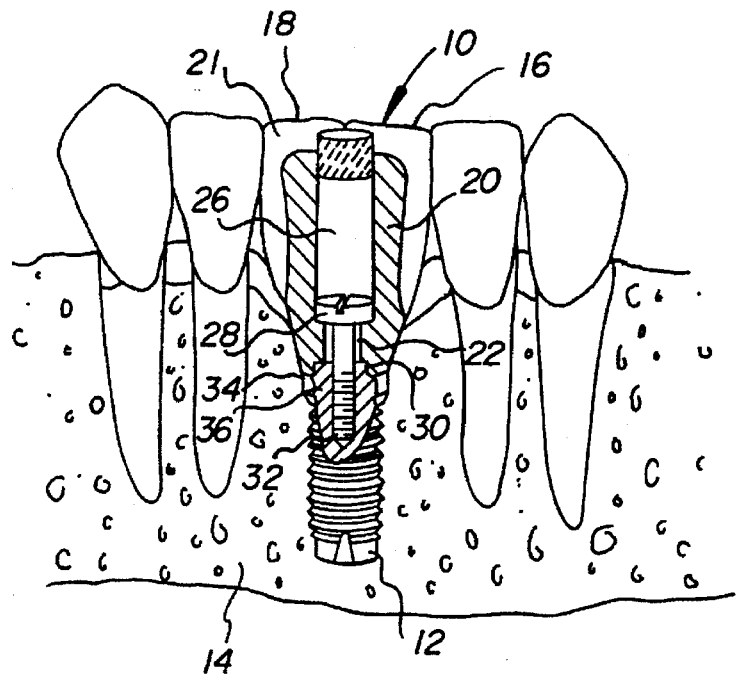
FIG. 1 is a schematic perspective view of a lower central prosthetic crown of the UCLA-type clinically attached to an implant fixture installed in the mouth of a patient.

FIG. 1 of the drawing illustrates a fixed dental prosthesis in the form of a crown 10 mounted on an implant fixture 12 that has been fixed in the bone 14 of a patient's jaw by the medium of osseointegration. For purpose of description, the illustrated prosthesis is of the UCLA-type and consists of the two central teeth 16 and 18 of the lower jaw. The crown 10 comprises a core and integrally formed abutment 20, typically formed of metal, usually gold, upon which is deposited a ceramic facing 21, typically porcelain, so-formed as to replicate the dentition to be restored. The abutment 20 contains a bore 22 adapted to receive the shank of a headed screw 24. The upper portion 26 of the bore 22 is of enlarged diameter to receive the head of the screw 24 and cooperates with the bore to define a shoulder 28 for seating the screw head. The lower portion of the bore is formed as a recess 30 complementary to the abutment-receiving portion of the implant fixture 12, which is typically formed as a headed cylinder having a threaded exterior to facilitate installation in a jaw bone and to assist in preventing retrograde movement of the implant fixture upon completion of osseointegration.

Figure 12:
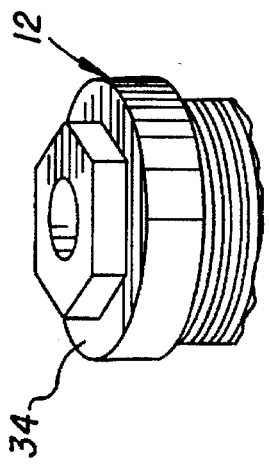
Figure 17:
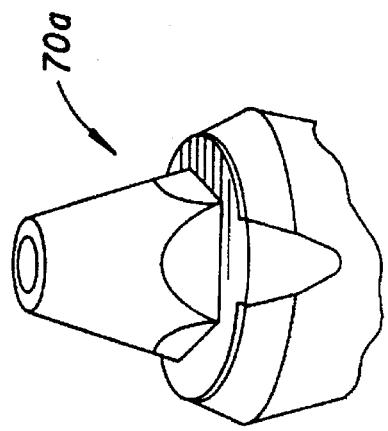
Figure 16:
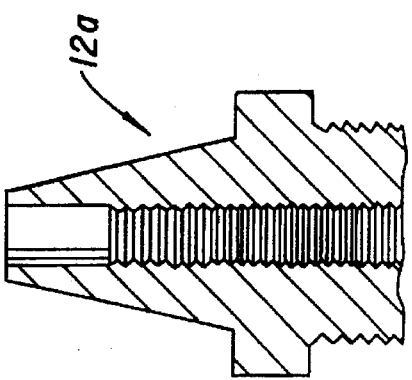
Figure 15:
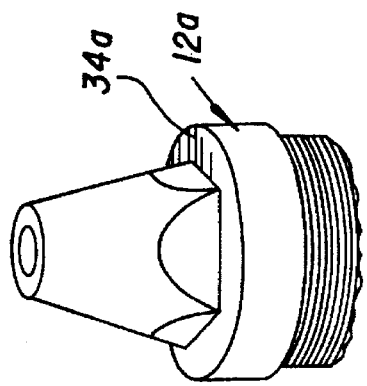
Figure 18:
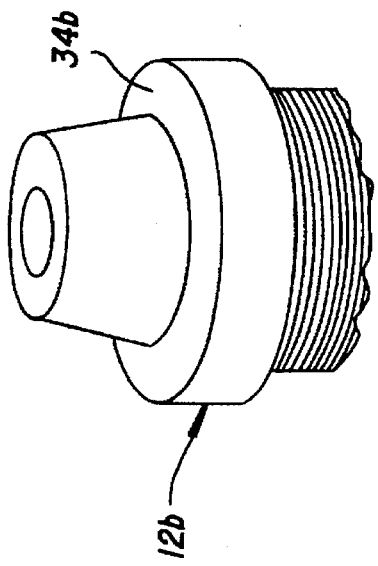
Figure 19:
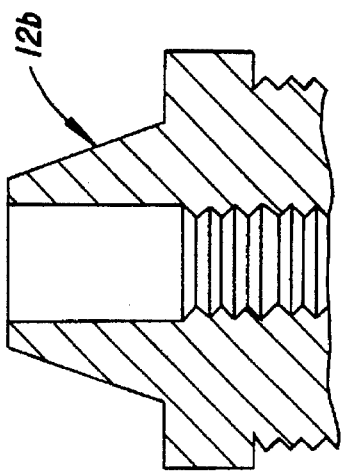
Figure 20:
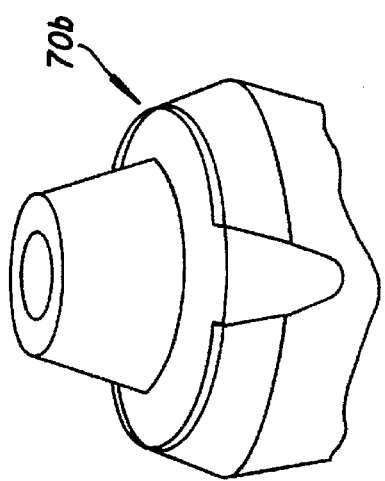
Figure 21:
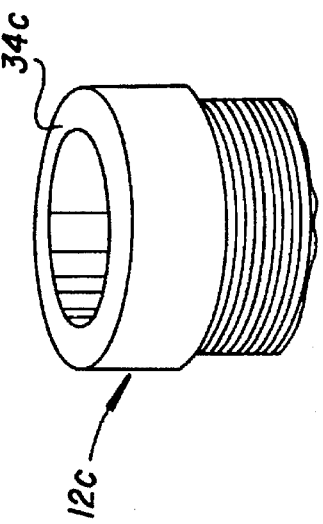
Figure 22:
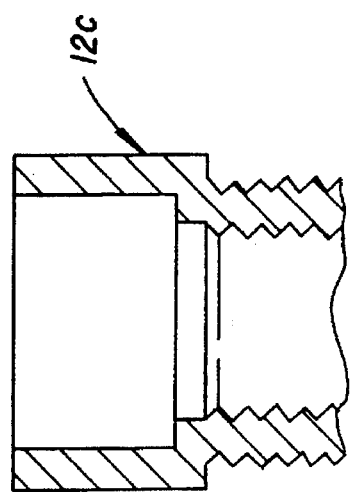
Figure 23:
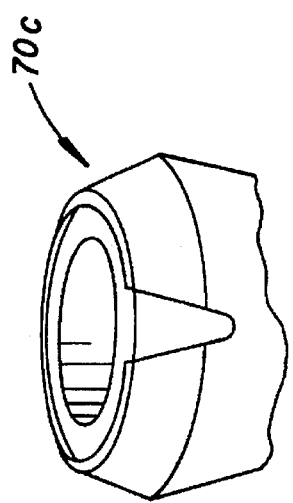
Figure 26:
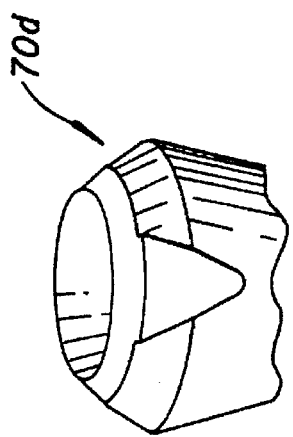
Figure 29:
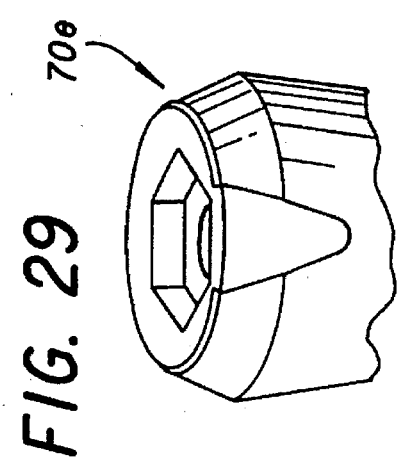
Figure 25:
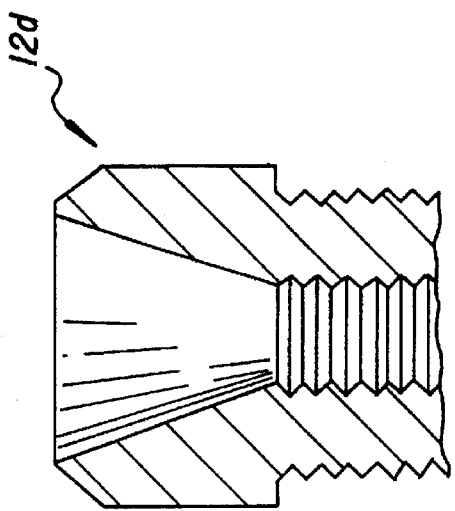
Figure 28:
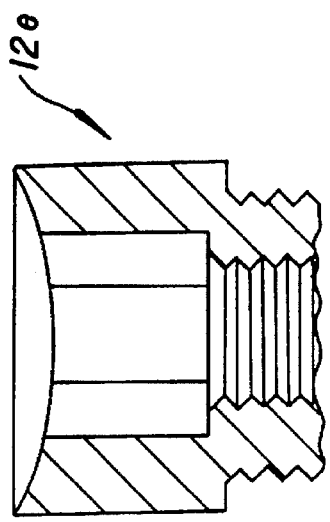
Figure 24:
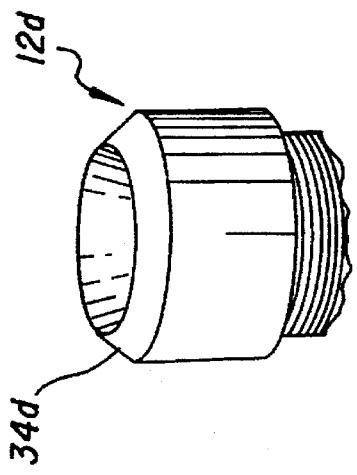
Figure 27:
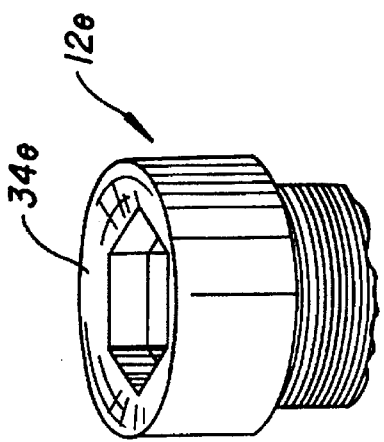
Figure 31:
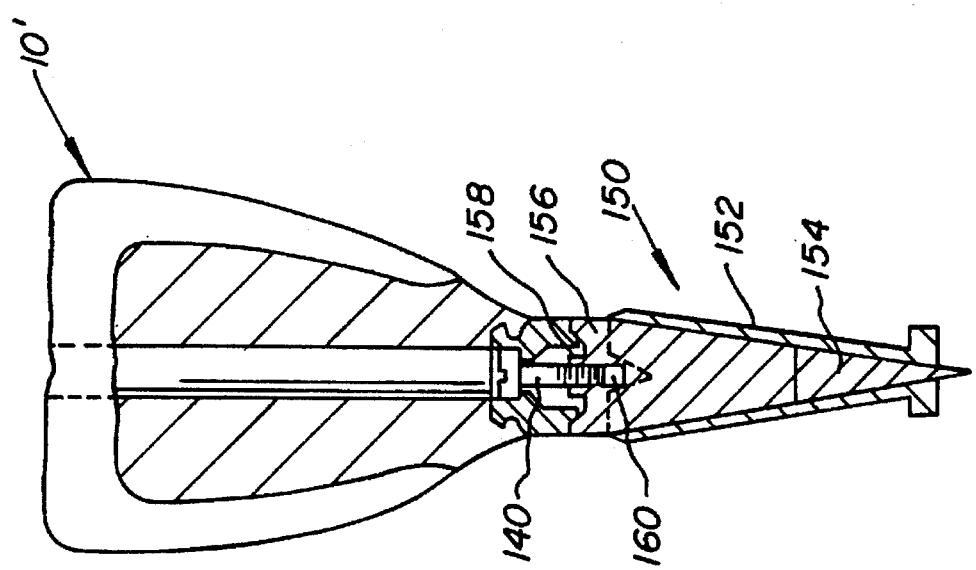
FIG. 31 is an illustration similar to FIG. 30 showing an implant analog assembly according to the invention for use with the crown prostheses of FIG. 30.

A socket 32 extends axially into the implant fixture 12 and is threaded for reception of the screw 24. In the illustrated device, the abutment-receiving portion of the implant fixture 12 is identified generally as 34 and is particularly structured, in cooperation with the recess 30, to seat the crown 10 in a manner to prevent rotational movement between it and the fixture. As shown, the abutment-receiving portion 34 of the implant fixture 12 contains a raised hexoganally-shaped boss 36, which is illustrated in greater detail in FIG. 12 and is intended for reception in the complementarily-shaped recess 30. It should be understood, however, that the instant invention is not limited to a particular abutment-receiving portion of an implant fixture, but, instead, as explained in more detail hereinafter, contemplates any and all of the currently known abutment-mounting configurations for implant fixtures suitable for use with the invention, as by the way of example but not by way of limitation, are shown in FIGS. 12 and 31 herein.

In restorative dentistry of the concerned type, it is necessary that an exact replica be made of the region of the patient's mouth in which the implant fixture 12 is installed and in which the crown 10 is to be mounted. Such replica is known as a "model" or "working model" and is typically formed of plaster-of-paris or die stone molded in a "negative" created by an impression taken of the concerned dentition in which the dentition is impressed in the impression material, that may comprise silicone rubber, or an equivalent moldable material, all as is generally known in the dental arts.

Figure 2:
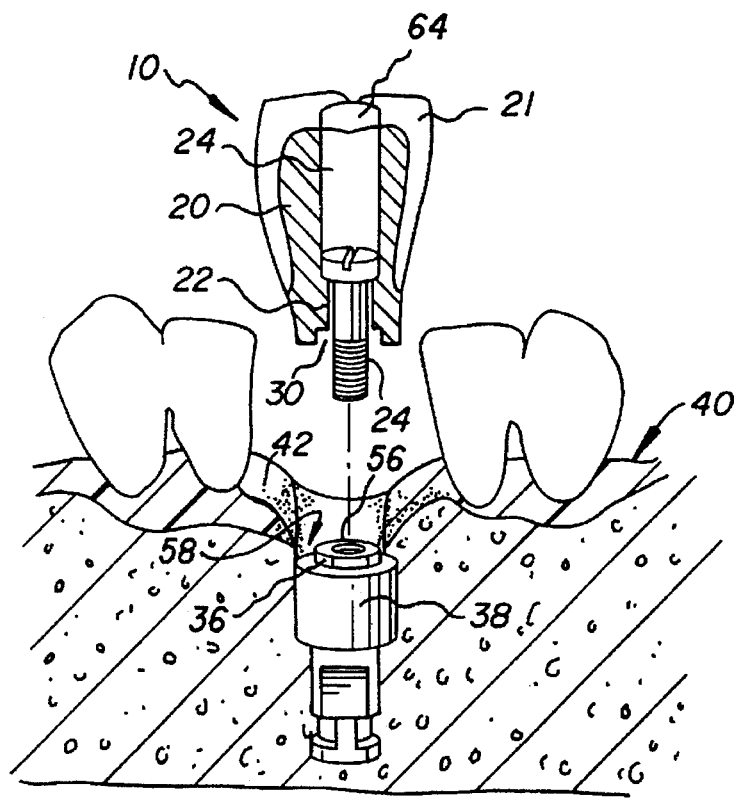
FIG. 2 is a schematic illustration of a prior art working model and laboratory analog for producing the prosthetic crown of FIG. 1.
Figure 4:
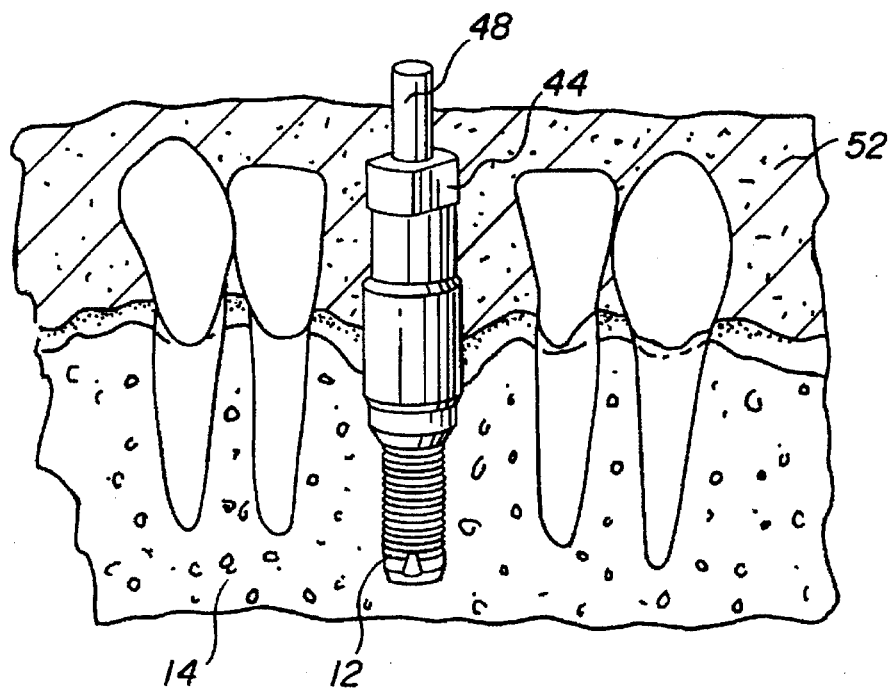
FIG. 4 is a schematic illustration of the initial step in the construction of the described working model involving the molding of a dental impression in the mouth of a patient.
Figure 5:
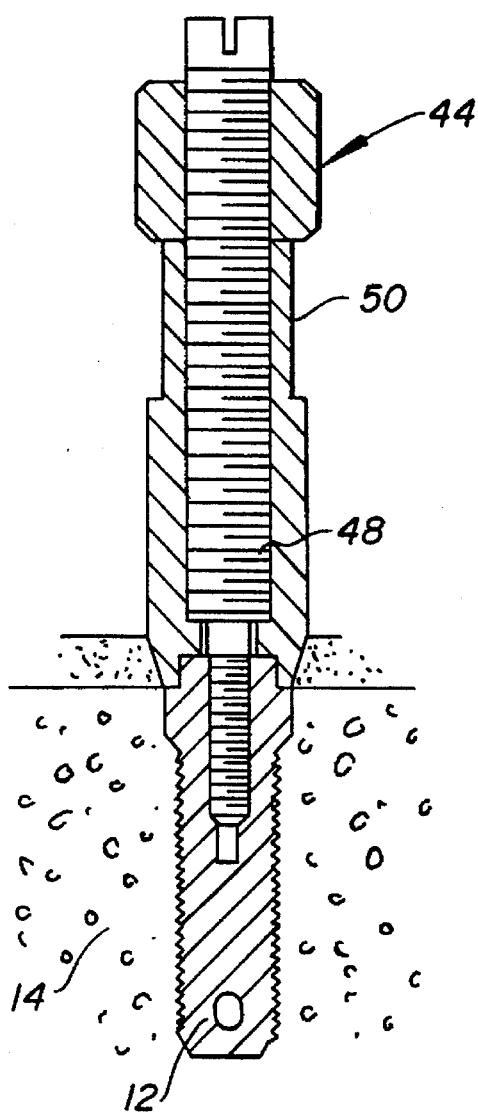
FIG. 5 is an enlarged partial sectional view of the step illustrated in FIG. 4 and showing an implant impression coping attached to an installed implant fixture.
Figure 6:
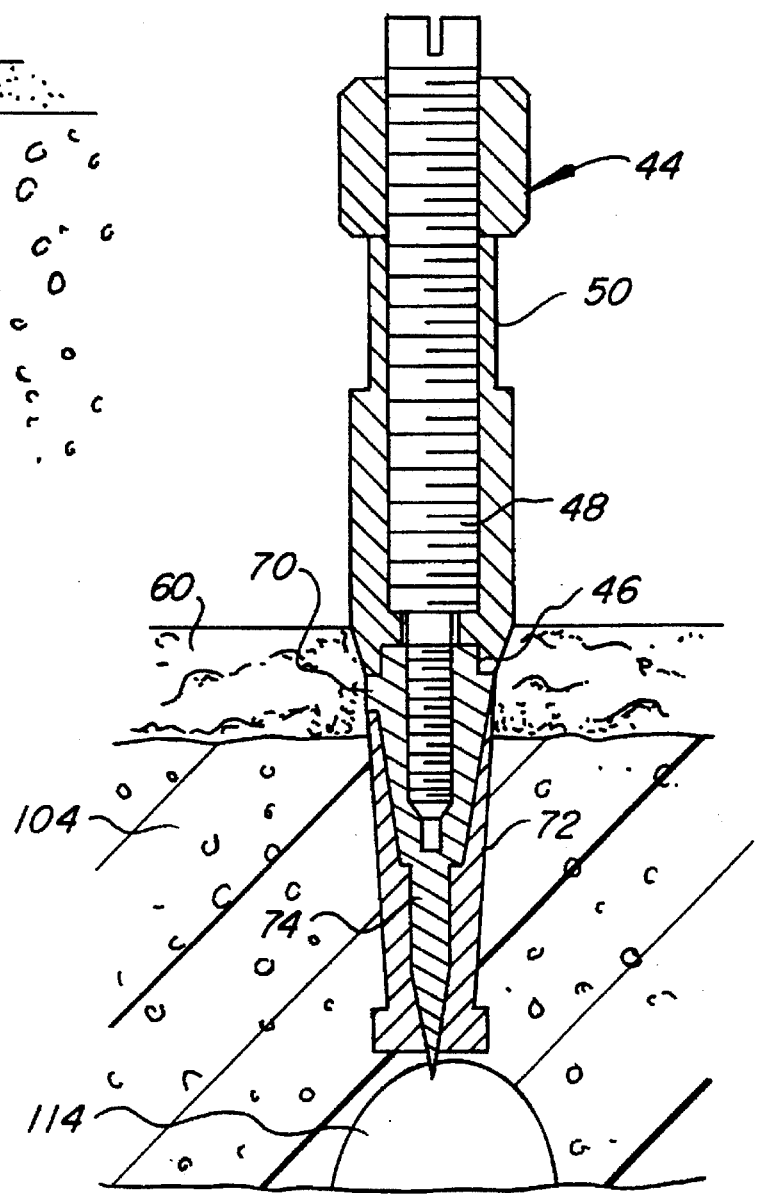
FIG. 6 is a view similar to FIG. 5 but showing a coping attached to an implant analog assembly in a working model according to the present invention.

FIG. 2 of the drawings shows a typical prior art model arrangement in which an implant laboratory analog 38 is embedded in a model 40 formed of plaster or die stone. A resilient layer formed of silicone-type material, is usually applied about the top of the analog 38 to replicate soft gum tissue. In order to form the model 40 according to prior art practice, an implant impression coping 44 is, as shown in FIGS. 4 and 5, attached in the patient's mouth to the previously installed implant fixture 12. The coping 44, which has at its lower end a complementary recess 46 to engage the abutment-receiving portion 34 of the implant fixture 12, is provided with a hollow interior for reception of an elongated coping screw 48 whose lower end is threaded and of a diameter to permit engagement with the threads in socket 32. The exterior surface of the coping 44 is preferably provided with means, here shown as opposed flats 50, to facilitate retention of the impression material 52 into which the patient's dentition, including the coping, is immersed (see FIG. 4) to make the "negative". Following set-up of the impression material, the formed impression 52 is invertedly inserted in an impression tray 54 with the coping 44 in place and the threads of the coping screw 48 exposed for reception of an implant analog 38 that is attached to the screw by means of engagement with the threaded socket 56 of the analog shown in FIG. 2.

Following the attachment of the analog 38 to the coping screw 48 in the impression 52, the impression is filled with a highly viscous molding material, in the form of moldable plaster or die stone, which, when hardened, creates the model arrangement shown in FIG. 2 wherein the implant analog 38, except for its upper surface 58, which replicates the abutment-receiving portion of the patient's implant fixture 12, is embedded. A soft tissue layer 60 having a through-hole 62 exposes the socket 56 in the analog upper surface 58. Thus, as shown in FIG. 2, the crown 10 is capable of being secured to model 40 by attachment to the exposed upper surface 58 of analog 38 by means of connection of a screw, identical to the implant screw 24, with the analog socket 56. Access for the screw 24 to the socket 56 is provided by the bore 22 in the crown abutment 20 and an opening 64 in the unfinished porcelain facing 21.

It will be appreciated that, in order for the laboratory technician to prepare the crown 10, which involves repeated installations and removals thereof to and from the model 40, the technician through the use of a tool, such as a screw driver (not shown), will either install or remove the screw 24, as the case may be.

When preparation of the crown 10 has been completed, an incision is made by the dentist in the gum tissue overlying the implant fixture 12 in the patient's mouth and the crown is attached to the fixture by threaded engagement of a screw 24 with the fixture socket 32. Finally, the opening 64 in the facing 21 is filled with porcelain filling material, or the like, to complete the restoration procedure.

The present invention provides an improved practice for the fabrication of a working model and an improved form of implant analog device for use in the working model and particularly adapted for the preparation of crowns intended for attachment to implant fixtures. According to the invention, the implant analog device of the prior art, such as that shown at 38 in FIG. 2, is replaced by an analog assembly identified generally by reference numeral 70, the details of which are best shown in FIGS. 7 and 8. As shown in these figures the analog assembly 70 comprises an elongated open-ended sleeve 72 which has conically tapered interior and exterior surfaces, 74 and 76 respectively. The lower, small diameter end of the sleeve contains an annular flange 78 concentric with the bottom opening 80 and operative to assist in preventing axial retrograde movement of the sleeve from the model. Similarly, the exterior surface 76 of the sleeve is provided intermediate its ends with a chordal flat 82 operative to prevent rotational movement of the sleeve within the model.

An analog pin 84 having a generally tapered exterior surface 86 is dimensioned to be snugly, slidingly received in the interior of the sleeve 72. The pin 82 is slightly longer in axial length than the sleeve 72 such that, when the pin is fully inserted in the sleeve, the lower end of the pin extends through the bottom opening 80 and beyond the end of the flange 78, as shown in FIG. 8. The surface of the pin 84, adjacent its lower end, contains a chordal flat 88 which cooperates with the chordal flat 82 on sleeve 72 to prevent relative rotational movement between the pin and sleeve. The pin is provided adjacent its upper end with a locator lug 90 which cooperates with a notch 92 designed to receive the lug recessed into the edge of the sleeve about its upper, greater diameter opening 94.

Figure 3:
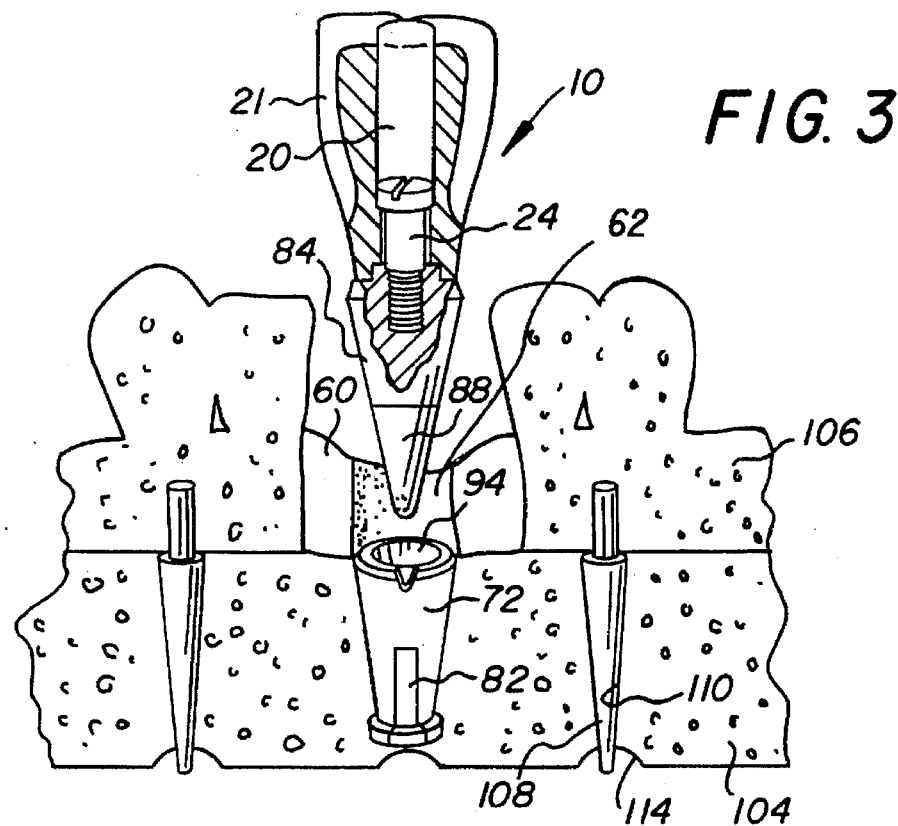
FIG. 3 is a schematic illustration of a working model and analog assembly constructed in accordance with the present invention for producing the prosthetic crown of FIG. 1.

The upper surface of the pin 84 defines an abutment-receiving portion 96 which replicates the abutment-receiving portion 34 of the implant fixture 12 to which the crown 12 will be prepared for application. Thus, there is provided on the upper surface of pin 84 raised hexagonal boss 98 though which an opening 100 to an axially disposed, threaded socket 102 extends. As shown best in FIG. 3, in the practice of the invention the crown 10 is fixedly secured to the pin 84 by means of screw 24. The configuration of the abutment-receiving portion 34, because it replicates the abutment-receiving portion on the implant fixture 12, is complementary to the recessed lower end of the crown abutment 20 and thereby adapted to be readily received in the recess 30 which, in the described embodiment, is hexagonally shaped. Consequently, for crown-preparation purposes the crown 10 can be readily manipulated between an installed condition in the model and a removed condition therefrom by simply sliding the pin 84 with attached crown 10 into and out of the sleeve 72.

To facilitate use of the described implant analog assembly in the working model, here generally referred to by reference numeral 40', the working model is formed as two detachable segments, a stationary segment 104 and a moveable segment 106. The latter segment 106 is adapted to be alignedly superimposed on the former segment 104 by the cooperation between alignment pins 108 fixedly set in segment 106 for reception in alignment holes 110 provided in segment 104.

Figure 9:
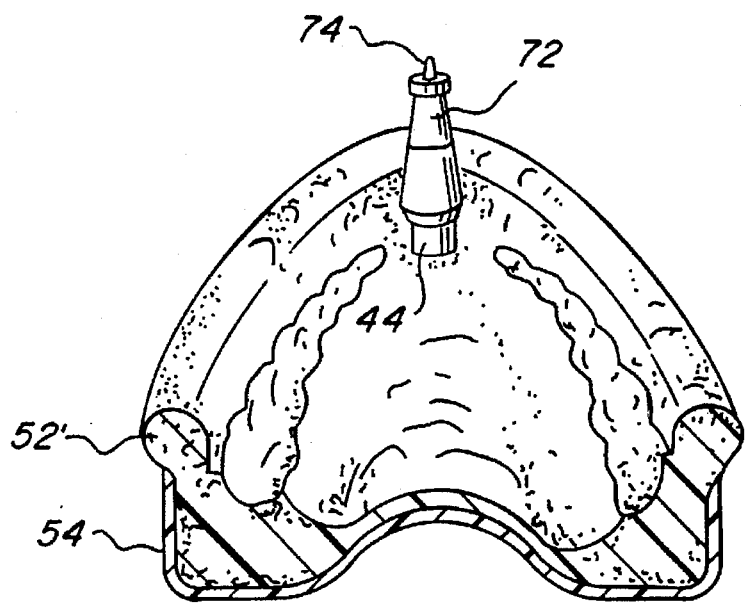
FIGS. 9, 10, and 11 illustrate an impression tray in progressive stages of working model production, FIG. 9 showing the impression tray with the formed impression received therein, FIG. 10 showing solidified die stone and "soft tissue" layer formed within the impression, and FIG. 11 showing a solidified layer of dental stone superimposed on the die stone.
Figure 10:
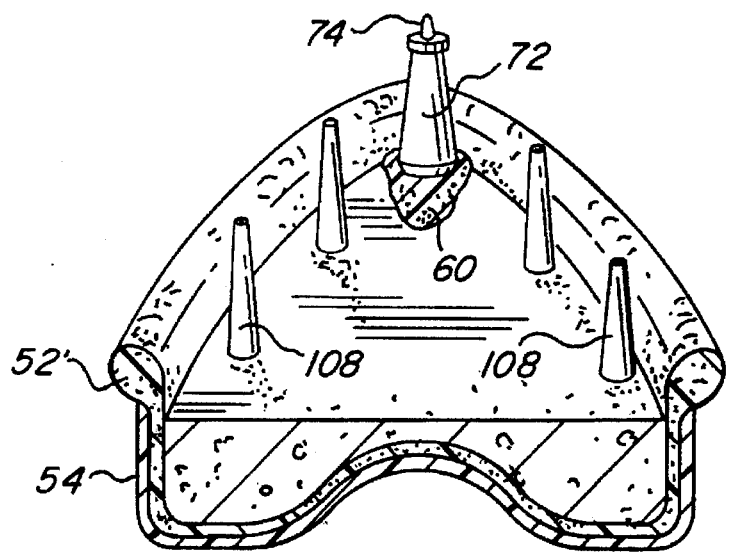
Figure 11:
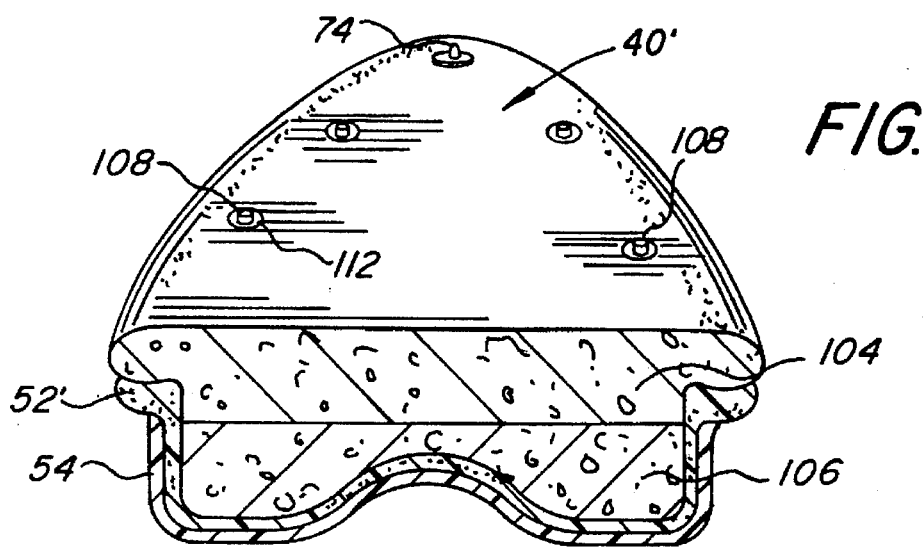
Figure 14:
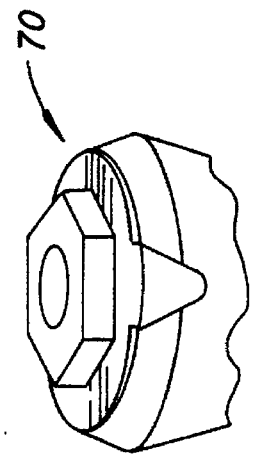
FIGS. 12 to 29 are illustrations showing, in sequence, a partial prospective representation of the abutment-receiving portion of an implant fixture, a partial elevational view, and a partial perspective representation of a replicated laboratory implant analog assembly according to the invention for several embodiments of implant analog assemblies contemplated by the invention.
Figure 13:
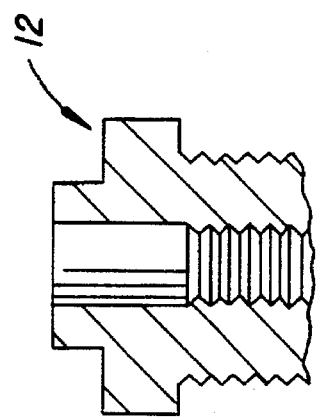

Construction of the model 40', the sequential steps of which are shown in FIGS. 9, 10, and 11, is distinguished from construction of the previously described conventional working model 40 to the extent that, prior to installing the formed impression 52' with attached coping 44 and coping screw 48 in the molding tray 54, the pin 84 of the implant analog assembly 70 is threadedly connected to the threaded end of the coping screw 48 and thereby securely fastened thereto and the analog sleeve 72 slidably placed upon the anchored pin (FIG. 9). Molding material, preferably die stone, is then packed into the formed impression 52 to a level slightly spaced below the inverted upper end of the sleeve 72 thereby forming, upon hardening, the movable segment 106 of working model 40'. Following solidification of the material forming the movable segment 106, a parting agent which may be any one or more of known types of such agents, such as soaps, waxes or silicones, is applied to the exposed surface of the segment 106 and of the alignment pins 108 and another layer of molding material is placed upon the segment 106, this layer being to a depth sufficient to substantially cover the alignment pins. (Typically, following application of the second layer of molding material, recess-producing forms 112 are placed in the surface of the molding material around the tips of the alignment pins 108 and the end of the analog pin 84, and the impression tray is inverted placing the second layer on a support surface whereupon any excess material which may extend beyond the peripheral edge of the tray is trimmed.) Following hardening of the second layer, the stationary model segment 104 is produced wherein, upon removal of the forms 112, recesses 114 are formed on the bottom surface of the segment whereupon the tips of pins 84 and 108 are accessible to assist in the case of pin 84 in releasing the crown-bearing analog pin during the preparation procedure and, in the case of pins 108, the separation of the respective model segments.

It will be appreciated that, by utilization of implant analog assemblies as described herein, in which the upper crown abutment-receiving surface of the pin substantially replicates the corresponding surface of the implant fixture previously installed in the patient's mouth, repeated removals and insertions, as are required by a laboratory technician during the course of preparation of the crown can be conducted easily and rapidly and without danger of damaging the model by erosion or breakage.

In FIGS. 12 to 29 of the drawings are shown various forms of abutment-receiving portions 34 and 34a through 34e of implant fixtures 12 and 12a through 12e, as well as implant analog assemblies 70 and 70a though 70e having abutment-receiving portions corresponding to those on the respective implant fixtures. It should be understood that the various forms of implant fixture abutment-receiving portions and corresponding replicated abutment-receiving portions on the analog pins of the respective implant analog assemblies are intended to be representative and not exhaustive of the forms which may be adopted for use with the invention.

Figure 30:
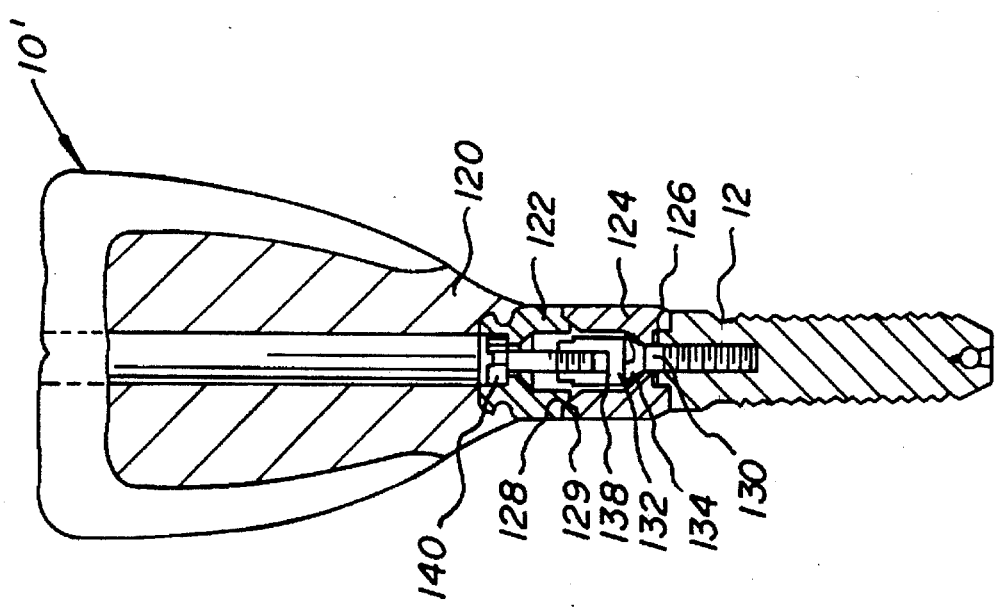
FIG. 30 is a partial sectional representation of a crown prostheses of the standard abutment and cylinder type installed on an implant fixture.

FIGS. 30 and 31 illustrate an embodiment of the invention in which the implant installation is of the standard abutment and cylinder assembly type wherein the crown 10' incorporates a core 120 having a cylinder 122 integrally formed at the base of the core. Intermediate the cylinder 122 and the implant fixture 12 is a separately-formed abutment 124 containing a hexagonal recess 126 for reception on the complementarily-formed head on the fixture. At its upper end the abutment 124 has a conically-formed recess 128 for receiving the self-centering conical end 129 of the cylinder 122. Connection of the abutment screw 130, whose enlarged head 132 contains a conical shoulder 134 adapted to seat on a cooperating shoulder in the bore of abutment 124, is provided with an internally threaded bore 138 adapted to receive a cylinder screw 140 for mounting the crown 10 on the implant fixture 12.

The implant analog assembly 150 shown in FIG. 31 for use in preparation of the crown 10' incorporates a sleeve 152 which corresponds in shape to the sleeve 72 of the earlier embodiments, 70 and 70a to 70e. The assembly pin 154, on the other hand, has an upper portion 156 that is axially elongated in order to replicate the abutment 124 and has an end face 158, which corresponds in shape to the combined upper ends of the abutment and abutment screw 130, having a threaded bore 160 that permits reception of the screw 140 for connecting the crown 10' to the pin 154. The structural configuration of the assembly 150 in other respects and its operation is the same as has been described above in connection with the implant abutment assembly 70.

It will be understood that various changes in the details, materials and arrangements of parts which have been herein described and illustrated in order to explain the nature of the invention, may be made by those skilled in the art within the principle and scope of the invention as expressed in the appended claims.

What is claimed is:

1. Method of producing a working model for preparation of a clinical crown for attachment to an implant fixture in a patient, comprising the steps of:

attaching a coping to the implant fixture mounted in the mouth of the patient;

pouring dental impression material about the selected region of the mouth of the patient to enclose said coping and the region of the mouth on adjacent sides thereof to form an impression mold;

removing an assemblage of the formed impression mold with the coping attached from the patient's mouth and connecting said assemblage to a model molding tray;

attaching to the exposed end of said coping an assembled separable analog pin and sleeve assembly;

packing molding material in said impression to a predetermined level leaving said analog sleeve exposed;

permitting said mold material to solidify to produce a movable model segment;

thereafter, placing additional molding material in said molding tray to substantially cover the exposed surface of the solidified movable model segment and said analog sleeve;

permitting said additional molding material to solidify to produce a stationary model segment;

removing said impression mold and said coping; and attaching a clinical crown to the pin element of said pin and sleeve assembly.

2. The method according to claim 1 including the step, prior to placing said additional molding material, of mounting positioning pins in the exposed surface of said movable model segment with their axes substantially parallel to the axis of said analog assembly.

3. The method according to claim 2 in which an abutment-receiving portion of the analog pin substantially replicates the corresponding portion of the implant fixture in the mouth of the patient, and including the step of providing said crown with an abutment sized to be received on said implant fixture, and attaching said crown to said pin employing a fastener connection corresponding to the fastener connection for connecting said crown to said implant fixture.

4. The method according to claim 3 including the steps of preparing said crown by removing said movable model segment from said stationary segment by slidingly moving said retention pins from receptor holes in said stationary segment.

5. The method according to claim 1 including the step, prior to placing said additional molding material, of applying separation material to said exposed surface of said solidified movable model segment.

6. The method according to claim 5 including the step prior to placing said additional molding material, of applying separation material to the exposed portions of said positioning pins.

7. The method according to claim 1 in which an abutment-receiving portion of the analog pin substantially replicates the corresponding portion of the implant fixture in the mouth of the patient, and including the step of providing said crown with an abutment sized to be received on said implant fixture, and attaching said crown to said pin employing as fastener connection corresponding to the fastener connection for connecting said crown to said implant fixture.

8. The method according to claim 7 including the steps of preparing said crown by axially slidingly removing and returning said analog pin and attached crown to and from said analog sleeve.

9. A working model for preparation of a clinical crown for attachment to an implant fixture installed in the mouth of a patient and containing and internally threaded socket for attachment of a crown, comprising:

a stationary segment and a movable segment, both formed of a solidified molding material;

said segments being connected for separation at a parting line therebetween;

an analog sleeve containing an axial bore fixedly secured on said stationary segment;

an analog pin axially slidably received in the bore of said analog sleeve, said pin having an external shape adapted for snug, slidable reception in said bore and at its upper end being formed to replicate a crown abutment-receiving portion of said implant fixture; and cooperable means on said pin and sleeve to prevent relative rotational movement between said pin and sleeve in their assembled condition.

10. A working model according to claim 9 in which the crown abutment-receiving portion of said analog pin contains an internally threaded socket for reception of a screw for attaching a clinical crown for processing to said pin.

11. A working model according to claim 10 in which said analog sleeve is open at its bottom end and said analog pin has a lower end extending beyond the bottom end of said analog sleeve; and a recess formed in a lower surface of said stationary segment beneath said open bottom end of said analog sleeve, whereby access to said lower end of said analog pin is provided.

12. A working model according to claim 10 including axially tapered positioning pins .attached to said movable segment at longitudinally spaced positions along said parting line and correspondingly tapered axial bores extending from said parting line into said stationary segment for snug releasable reception of said positioning pins.

13. A working model according to claim 12 including a void in the solidified molding material of said movable segment, said void being disposed in overlying relation to said analog pin to permit access and removal of said analog pin from said analog sleeve.

14. A working model according to claim 13 in which said abutment-receiving portion of said analog pin includes means forming a shoulder on said pin to restrict axial movement thereof within the bore of said analog sleeve; and means forming a surface disposed externally of said bore for reception of the abutment of said crown.

15. A working model according to claim 14 in which said abutment-receiving surface on said analog pin contains a projection forming a male element for reception of a female element of a crown abutment.

16. A working model according to claim 14 in which said abutment-receiving surface on said analog pin contains a recess forming a female element for reception of a male element of a crown abutment.

17. A working model according to claim 10 in which said analog sleeve has an axially tapered bore and said analog pin has a correspondingly tapered external surface for snug, sliding reception in said analog sleeve bore; and cooperating flats formed on said analog sleeve and said analog pin to prevent relative rotational movement therebetween.

18. A laboratory analog for installation in a working model for preparation of a clinical crown intended for attachment to an implant fixture installed in the mouth of a patient, comprising:

an analog sleeve having an external surface configured for locked retention in a body of solidified molding material and an axially-extending bore;

an analog pin having an external shape for snug, sliding reception to a predetermined extent in the bore of said analog sleeve;

cooperating elements on said analog sleeve and said analog pin to prevent relative rotation therebetween; and an abutment-receiving portion on an exposed, crown-receiving end of said pin, and means in said abutment-receiving portion for attaching a clinical crown thereto, said means substantially replicating a means for attaching said crown to said implant fixture and including an axially disposed, internally threaded bore for reception of a crown-attaching screw, said bore opening at the substantial axial center of said abutment-receiving portion of said analog pin.

19. A laboratory analog according to claim 18 in which said internal bore of said analog sleeve and said external surface of said analog pins are axially tapered; and said rotation-restricting elements include cooperating flats formed on said bore and the surface of said pin for mutual engagement when said analog pin is installed in said analog sleeve.

20. A laboratory analog according to claim 18 in which said analog sleeve has an open bottom and said analog pin has an axial end that protrudes from said sleeve bottom when said pin is installed in said sleeve.

21. A laboratory analog according to claim 18 in which said abutment-receiving portion of said analog pin includes means forming a shoulder on said pin to restrict axial movement thereof within the bore of said analog sleeve; and means forming a surface disposed externally of said bore for reception of the abutment of said crown.

22. A laboratory analog according to claim 21 in which said abutment-receiving surface on said analog pin contains a projection forming a male element for reception of a female element of a crown abutment.

23. A laboratory analog for installation in a working model for preparation of a clinical crown intended for attachment to an implant fixture installed in the mouth of a patient, comprising:

an analog pin having an external shape for snug, sliding reception to a predetermined extent in a bore formed in said working model;

cooperating elements on said bore and said analog pin to prevent relative rotation therebetween;

an abutment-receiving portion on an exposed, crown-receiving end of said pin replicating a crown-receiving portion of said installed implant fixture; and means in said abutment-receiving portion for attaching a clinical crown thereto, said means substantially replicating a means for attaching said crown to said implant fixture.

24. A laboratory analog according to claim 23 in which said crown-attaching means comprises an axially disposed, internally threaded bore for reception of a crown-attaching screw, said bore opening at the substantial axial center of said abutment-receiving portion of said analog pin.

25. A laboratory analog according to claim 23 in which said bore and said external surface of said analog pin are axially tapered; and said rotation-restricting elements include cooperating flats formed on said bore and the surface of said pin for mutual engagement when said analog pin is installed in said working model.

26. A laboratory analog according to claim 23 in which said abutment-receiving portion of said analog pin includes means forming a shoulder on said pin to restrict axial movement thereof within the bore of said working model; and means forming a surface disposed externally of said bore for reception of the abutment of said crown.

27. A laboratory analog according to claim 26 in which said abutment-receiving surface on said analog pin contains a projection forming a male element for reception of a female element of a crown abutment.

28. A laboratory analog according to claim 26 in which said abutment-receiving surface on said analog pin contains a recess forming a female element for reception of a male element of a crown abutment.

29. A laboratory analog for installation in a working model for preparation of a clinical crown intended for attachment to an implant fixture installed in the mouth of a patient, comprising:

an analog sleeve having an external surface configured for locked retention in a body of solidified molding material and an axially-extending bore;

an analog pin having an external shape for snug, sliding reception to a predetermined extent in the bore of said analog sleeve;

cooperating elements on said analog sleeve and said analog pin to prevent relative rotation therebetween; and an abutment-receiving portion on an exposed, crown-receiving end of said pin and including means forming a shoulder on said pin to restrict axial movement thereof within the bore of said analog sleeve; and means in said abutment-receiving portion for attaching a clinical crown thereto, said means substantially replicating a means for attaching said crown to said implant fixture and including a surface disposed externally of said bore for reception of the abutment of said crown, said surface containing a recess forming a female element for reception of a male element of a crown abutment.

* * * * *